United States Patent
Yamaki et al.

(10) Patent No.: US 9,506,854 B2
(45) Date of Patent: Nov. 29, 2016

(54) METHOD AND DEVICE FOR MEASURING SCATTERING-ABSORPTION BODY

(75) Inventors: Etsuko Yamaki, Hamamatsu (JP);
Yutaka Yamashita, Hamamatsu (JP);
(Continued)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 617 days.

(21) Appl. No.: 13/695,362

(22) PCT Filed: Mar. 29, 2011

(86) PCT No.: PCT/JP2011/057871
§ 371 (c)(1),
(2), (4) Date: Jan. 10, 2013

(87) PCT Pub. No.: WO2011/135965
PCT Pub. Date: Nov. 3, 2011

(65) Prior Publication Data
US 2013/0100449 A1 Apr. 25, 2013

(30) Foreign Application Priority Data
Apr. 30, 2010 (JP) .................................. 2010-105526

(51) Int. Cl.
*G01N 21/17* (2006.01)
*G01N 21/49* (2006.01)
(Continued)

(52) U.S. Cl.
CPC ............. *G01N 21/17* (2013.01); *A61B 5/1455* (2013.01); *G01N 21/359* (2013.01); *G01N 21/49* (2013.01);
(Continued)

(58) Field of Classification Search
CPC ........... A61B 5/00; A61B 6/00; A61B 5/1455; A61B 5/14546; A61B 2562/0242; G01N 21/49; G01N 21/359
USPC ........................................................ 600/473
See application file for complete search history.

(56) References Cited

U.S. PATENT DOCUMENTS

| 2009/0209836 A1* | 8/2009 | Niwayama ......... A61B 5/14551 600/324 |
| 2010/0016732 A1* | 1/2010 | Wells .................. A61B 5/0059 600/476 |

FOREIGN PATENT DOCUMENTS

| CN | 1542434 | 11/2004 |
| CN | 1580740 | 2/2005 |

(Continued)

OTHER PUBLICATIONS

Yamamoto, Katsuyuki et al., "Accurate NIRS measurement of muscle oxygenation by correcting the influence of a subcutaneous fat layer", Proc. SPIE 3194, Photon Propagation in Tissues III, 166 (Jan. 1, 1998).*

(Continued)

Primary Examiner — Tse Chen
Assistant Examiner — Charles G Chiang
(74) Attorney, Agent, or Firm — Drinker Biddle & Reath LLP

(57) ABSTRACT

Light irradiates one light incident position on the surface of a scattering-absorption body. The light that propagates through the interior of the scattering-absorption body is detected at one light detecting position on the surface of the scattering-absorption body. On the basis of a light detection signal, a temporal profile of the light intensity of the detected light is acquired, and on the basis of the temporal profile, an mean optical path length of the light in the interior of the scattering-absorption body and information relating to the amount of substance to be measured in a region to be (Continued)

measured are calculated. The information relating to the amount of substance to be measured is corrected on the basis of the mean optical path length, such that the longer the mean optical path length, the greater the amount of substance to be measured is.

14 Claims, 15 Drawing Sheets

(75) Inventors: Motoki Oda, Hamamatsu (JP); Hiroaki Suzuki, Hamamatsu (JP); Toshihiko Suzuki, Hamamatsu (JP); Hiroshi Watanabe, Hamamatsu (JP); Shunsaku Koga, Kobe (JP)

(51) Int. Cl.
*A61B 5/1455* (2006.01)
*G01N 21/359* (2014.01)
*A61B 5/145* (2006.01)

(52) U.S. Cl.
CPC .... *A61B 5/14546* (2013.01); *A61B 2562/0242* (2013.01)

(56) References Cited

FOREIGN PATENT DOCUMENTS

| | | |
|---|---|---|
| CN | 1600271 | 3/2005 |
| JP | 2001-133396 | 5/2001 |
| JP | 2003-202287 | 7/2003 |
| JP | 2004-73559 | 3/2004 |
| JP | 2005-111165 | 4/2005 |
| JP | 2005-114678 | 4/2005 |

OTHER PUBLICATIONS

Takafumi Hamaoka et al., "Near-infrared spectroscopy/imaging for monitoring muscle oxygenation and oxidative metabolism in healthy and diseased humans," Journal of Biomedical Optics, Nov./Dec. 2007, pp. 062105-1-062105-16, vol. 15, No. 6.

Masatsugu Niwayama et al., "Quantitative measurement of muscle hemoglobin oxygenation using near-infrared spectroscopy with correction for the influence of a subcutaneous fat layer," Review of Scientific Instruments, Dec. 2000, pp. 4571-4575, vol. 71, No. 12.

Maria Angela Franceschini et al., "Influence of a superficial layer in the quantitative spectroscopic study of strongly scattering media," Applied Optics, Nov. 1, 1998, pp. 7447-7458, vol. 37, No. 31.

Ömer Şayli et al., "Crosstalk and error analysis of fat layer on continuous wave near-infrared spectroscopy measurements," Journal of Biomedical Optics, Nov./Dec. 2008, pp. 064019-1-064019-11, vol. 13, No. 6.

Li Jian-ping et al., "Validity of the Diffusion Approximation in Determining the Optical Properties of Biological Tissus," J. Applied Optics, vol. 26(1), Jan. 31, 2005, pp. 20-24.

Wu Tai-hu, et al., "A Study of Non-invasive Measurement of Human Hemoglobin Concentration by Near Infrared Spectroscopy," ACTA Laser Biology Sinica, vol. 15(2), Apr. 30, 2006, pp. 204-208.

* cited by examiner

Fig.10

| No. | MEAN OPTICAL PATH LENGTH [cm] | INTERVENING TISSUE THICKNESS [cm] | MEASUREMENT SENSITIVITY S |
|---|---|---|---|
| 1 | 12.77 | 0.42 | 0.443 |
| 2 | 14.86 | 0.53 | 0.281 |
| 3 | 15.61 | 0.57 | 0.233 |
| 4 | 12.59 | 0.41 | 0.459 |
| 5 | 12.81 | 0.42 | 0.440 |
| 6 | 13.48 | 0.46 | 0.384 |
| 7 | 13.25 | 0.45 | 0.403 |
| 8 | 13.55 | 0.46 | 0.379 |
| 9 | 11.86 | 0.38 | 0.525 |
| 10 | 12.79 | 0.42 | 0.442 |
| 11 | 14.74 | 0.52 | 0.289 |
| 12 | 13.24 | 0.45 | 0.404 |
| 13 | 13.36 | 0.45 | 0.394 |
| 14 | 13.38 | 0.45 | 0.392 |

(a)

(b)

METHOD AND DEVICE FOR MEASURING SCATTERING-ABSORPTION BODY

TECHNICAL FIELD

The present invention relates to a method and a device for measuring information relating to the amount (concentration) of a substance in a scattering-absorption body, for instance hemoglobin in blood.

BACKGROUND ART

Patent Literature 1 discloses a method for non-invasively measuring the interior of a scattering-absorption body. In this measurement method, light incidence means causes pulsed light to irradiate, at a light incidence position, a scattering-absorption body that comprises a region to be measured and a region not to be measured. The pulsed light, while being scattered, reaches then a light detecting position, through respective optical paths, and is detected by light detecting means. At least one from among the light incident position and the light detecting position is a plurality of positions. The variation amount of the absorption coefficient of the region to be measured alone is calculated by using a temporal profile of the detected light and assuming that the partial optical path length of propagation through the region not to be measured is constant, irrespective of the optical path.

Non Patent Literature 1 indicates that in measurements by near-infrared spectroscopy (NIRS) the mean optical path length of light that propagates through the body varies depending on tissular structure, i.e. muscle or fat, the amount of blood and muscle morphology.

Non Patent Literature 2 discloses the feature of measuring beforehand fat thickness by a separate method, and correcting then, according to that fat thickness, measurement results of hemoglobin amount by near-infrared spectroscopy.

CITATION LIST

Patent Literature

Patent Literature 1: Japanese Patent Application Publication No. 2003-202287

Non Patent Literature

Non Patent Literature 1: Takafumi Hamaoka et al., 'Near-infrared spectroscopy/imaging for monitoring muscle oxygenation and oxidative metabolism in healthy and diseased humans', Journal of Biomedical Optics 12(6), 062105 (November/December 2007)

Non Patent Literature 2: Niwayama, Masatsugu et al., 'Quantitative measurement of muscle hemoglobin oxygenation using near-infrared spectroscopy with correction for the influence of a subcutaneous fat layer', Review of Scientific Instruments, Vol. 71, No. 12, pp. 4571-4575 (2000)

SUMMARY OF INVENTION

Technical Problem

In non-invasive measurement of a scattering-absorption body using light, the scattering-absorption body may in some instances comprise, besides the region to be measured, also a region not to be measured (intervening tissue) that is interposed between the region to be measured and the epidermis. For instance, in the case of a hemodynamic evaluation of muscle by near-infrared spectroscopy, fat that covers muscle is treated as intervening tissue that is not to be measured, and muscle is treated as the region to be measured, given that the amount of blood in fat is significantly smaller than in muscle.

In order to measure the scattering-absorption body non-invasively, however, light must irradiate the region to be measured and be detected by way of the intervening tissue. As a result, variability arises in the measurement result depending on the thickness of the intervening tissue. This constitutes one factor that impairs measurement precision. FIG. 15(a) and FIG. 15(b) are diagrams illustrating schematically the internal structure of a scattering-absorption body 100. In the figures, the scattering-absorption body 100 comprises a region to be measured 101 and an intervening tissue 102. FIG. 15(a) illustrates an instance where the intervening tissue 102 is thicker than in FIG. 15(b).

In a case where, as illustrated in FIG. 15(b) the thickness t of the intervening tissue 102 is small, the greater part of the optical path length of light P that irradiates the scattering-absorption body 100 is encompassed within the region to be measured 101. Therefore, measured values are obtained that are close to the right values. However, the proportion of the portion of passage through the intervening tissue 102, in the optical path length of light P that irradiates into the scattering-absorption body 100, increases when the thickness t of the intervening tissue 102 is substantial, as illustrated in FIG. 15(a). Thus, the thicker the intervening tissue 102, the shorter becomes the partial optical path length of passage through the region to be measured 101, and hence a measured value is calculated that is smaller than the right value.

Non Patent Literature 1 described above does not indicate what kind of relationship exists between fat thickness and mean optical path length. The method set forth in Non Patent Literature 2 is problematic in that the fat thickness of a measurement site must be measured beforehand for each subject, which makes for a complex measurement.

It is thus an object of the present invention to provide a method and device for measuring a scattering-absorption body that enable measurement results, having had the influence of intervening tissue excluded therefrom, to be obtained in accordance with a simple method.

Solution to Problem

In order to solve the above problems, the method for measuring a scattering-absorption body in an aspect of the present invention is a method for measuring, non-invasively, information relating to an amount of substance to be measured at a region to be measured of a scattering-absorption body that contains the region to be measured and an intervening tissue that is present between the region to be measured and a surface of the scattering-absorption body, the method comprising: (a) a light incidence step of causing light of a predetermined wavelength to be incident, through one light incident position that is set on the surface of the scattering-absorption body; (b) a light detection step of obtaining a light detection signal by detecting the light of the predetermined wavelength that propagates through the interior of the scattering-absorption body, at one light detecting position that is set on the surface of the scattering-absorption body; (c) a signal processing step of acquiring a temporal profile of light intensity of detected light, on the basis of the light detection signal; and (d) a calculation step of calculating, on the basis of the temporal profile, an mean optical path length of light of the predetermined wavelength in the interior of the scattering-absorption body, and the information relating to the amount of substance to be measured in the region to be measured; wherein in the calculation step, the information relating to the amount of substance to be measured is corrected on the basis of the mean optical path length, such that the longer the mean optical path length, the greater the amount of substance to be measured is. The device for measuring a scattering-absorption body in an aspect of the present invention is a device that measures, non-invasively, information relating to an amount of substance to be measured at a region to be measured of a scattering-absorption body that comprises the region to be measured and intervening tissue that is present between the region to be measured and a surface of the scattering-absorption body, the device comprising: (a) light incident means for causing light of a predetermined wavelength to be incident, through one light incident position that is set on the surface of the scattering-absorption body; (b) light detecting means for generating a light detection signal by detecting light of the predetermined wavelength that propagates through the interior of the scattering-absorption body, at one light detecting position that is set on the surface of the scattering-absorption body; (c) signal processing means for acquiring a temporal profile of light intensity of detected light, on the basis of the light detection signal; and (d) calculation means for calculating, on the basis of the temporal profile, an mean optical path length of light of the predetermined wavelength in the interior of the scattering-absorption body, and the information relating to the amount of substance to be measured in the region to be measured. The calculation means corrects the information relating to the amount of substance to be measured on the basis of the mean optical path length, such that the longer the mean optical path length, the greater the amount of substance to be measured is.

As a result of diligent research, the inventors found that a distinctive correlation exists between mean optical path length and intervening tissue thickness. Therefore, the influence of intervening tissue can be easily excluded by correcting the measurement result (information relating to the amount of substance to be measured) on the basis of the mean optical path length. That is, the method and device for measuring a scattering-absorption body that enable measurement results, having had the influence of intervening tissue excluded therefrom, to be obtained in accordance with a simple method. Herein, information relating to the amount of substance to be measured denotes the number of substances to be measured, concentration, time variation amount, and other magnitudes.

In the calculation step in the method for measuring a scattering-absorption body, the information relating to the amount of substance to be measured may be corrected on the basis of a correlation, acquired beforehand, between the mean optical path length and the thickness of the intervening tissue. The calculation means of the device for measuring a scattering-absorption body may correct the information relating to the amount of substance to be measured on the basis of a correlation, acquired beforehand, between the mean optical path length and the thickness of the intervening tissue. The information relating to the amount of substance to be measured can be appropriately corrected as a result. In this case, the correlation between the mean optical path length and the thickness of the intervening tissue may be a relationship in which the longer the mean optical path length, the thicker the intervening tissue is.

In the calculation step in the method for measuring a scattering-absorption body, the information relating to the amount of substance to be measured may be corrected on the basis of an optical path length per unit thickness of intervening tissue acquired beforehand. Likewise, the calculation means of the device for measuring a scattering-absorption body may correct the information relating to the amount of substance to be measured on the basis of the optical path length per unit thickness of intervening tissue, acquired beforehand. The optical path length per unit thickness of intervening tissue is obtained on the basis of a relationship between a variation amount of the substance to be measured and the thickness of the intervening tissue at a time where only the substance to be measured is caused to vary. Alternatively, in the method for measuring a scattering-absorption body, in the calculation step, the information relating to the amount of substance to be measured may be corrected on the basis of a correlation, acquired beforehand, between the mean optical path length and measurement sensitivity. Likewise, in the device for measuring a scattering-absorption body, the calculation means may correct the information relating to the amount of substance to be measured on the basis of a correlation, acquired beforehand, between the mean optical path length and measurement sensitivity. In the calculation step of the method for measuring a scattering-absorption body, the correlation between the mean optical path length and the measurement sensitivity may be worked out from the mean optical path length and an optical path length of a portion of passage through the region to be measured or the intervening tissue, within the mean optical path length in the interior of the scattering-absorption body. Likewise, the calculation means of the device for measuring a scattering-absorption body may work out the correlation between the mean optical path length and the measurement sensitivity from the mean optical path length and an optical path length of a portion of passage through the region to be measured or the intervening tissue, within the mean optical path length in the interior of the scattering-absorption body. The information relating to the amount of substance to be measured can be appropriately corrected as a result of any of the foregoing.

In the calculation step of the method for measuring a scattering-absorption body, the optical path length of a portion of passage through the intervening tissue, within the mean optical path length in the interior of the scattering-absorption body, may be estimated on the basis of an optical path length per unit thickness of the intervening tissue, and a thickness of the intervening tissue obtained from a correlation between, acquired beforehand, the thickness of the intervening tissue and the mean optical path length; the measurement sensitivity may be worked out from the estimated optical path length; and the information relating to the amount of substance to be measured may be corrected using the measurement sensitivity. Likewise, the calculation means of the device for measuring a scattering-absorption body may estimate the optical path length of a portion of passage through the intervening tissue, within the mean optical path length in the interior of the scattering-absorption body, on the basis of an optical path length per unit thickness of the intervening tissue, and a thickness of the intervening tissue obtained from a correlation acquired beforehand, between the thickness of the intervening tissue and the mean optical path length; may work out the measurement sensitivity from the estimated optical path length; and may correct the information relating to the amount of substance to be measured using the measurement sensitivity.

In the method for measuring a scattering-absorption body and the device for measuring a scattering-absorption body, the region to be measured may be muscle and the intervening tissue may be fat.

Advantageous Effects of Invention

The method and device for measuring a scattering-absorption body of the present invention enable measurement results, having had the influence of intervening tissue excluded therefrom, to be obtained in accordance with a simple method.

BRIEF DESCRIPTION OF DRAWINGS

FIG. 10 is a chart illustrating mean optical path length, intervening tissue thickness estimated from mean optical path length, and measurement sensitivity estimated from a partial optical path length, for 14 individuals;

DESCRIPTION OF EMBODIMENTS

Figure 1:
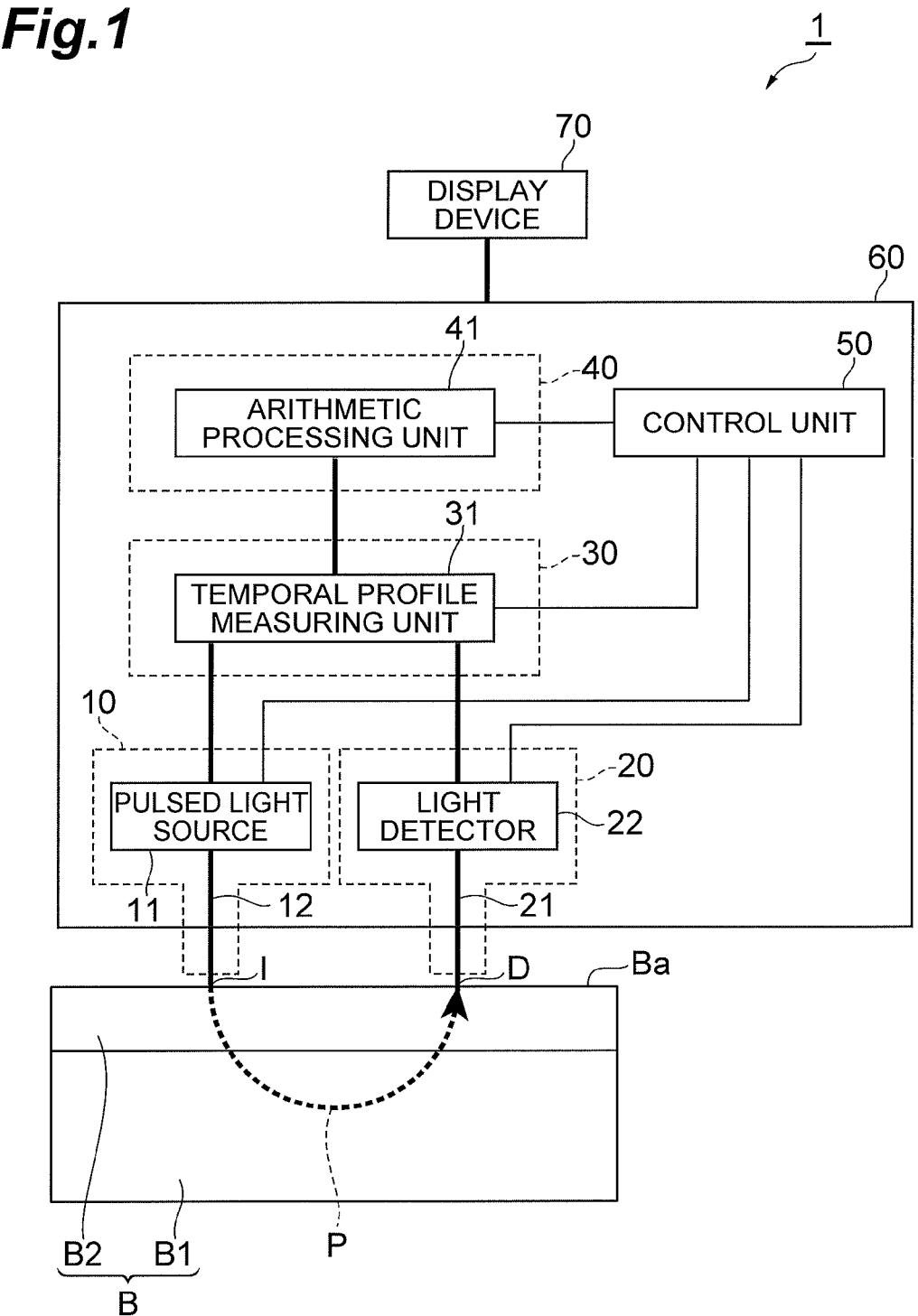
FIG. 1 is a block diagram illustrating schematically the configuration of an embodiment of a device for measuring a scattering-absorption body that is used appropriately for carrying out the method for measuring a scattering-absorption body according to the present invention.

Embodiments of the method and device for measuring a scattering-absorption body will be explained next with reference to accompanying drawings. In the explanation of the figures, identical elements will be denoted by identical reference numerals, and a recurrent explanation thereof will be omitted.

FIG. 1 is a block diagram illustrating schematically the configuration in one embodiment of a device for measuring a scattering-absorption body that is used appropriately for carrying out a method for measuring a scattering-absorption body. The device for measuring a scattering-absorption body 1 is a device for calculating information (quantity, variation amount, concentration and the like) relating to a substance to be measured (oxyhemoglobin and deoxyhemoglobin) comprised in tissue of a scattering-absorption body (living tissue) B. The scattering-absorption body B comprises a region to be measured B1 (for instance, muscle) and intervening tissue B2 (for instance fat) that is interposed between the region to be measured B1 and a surface Ba of the scattering-absorption body B. The intervening tissue B2 holds little blood, and hence most of the substance to be measured is present in the region to be measured B1. The device for measuring a scattering-absorption body 1 calculates information relating to the amount of substance to be measured that is present in the region to be measured B1.

The device for measuring a scattering-absorption body 1 illustrated in FIG. 1 comprises a main body 60 and a display unit 70. The main body 60 comprises light incident means 10, light detecting means 20, signal processing means 30, calculation means 40 and control unit 50 that controls the foregoing.

The light incident means 10 is a means for causing pulsed light P of a predetermined wavelength to be incident through a light incident position I of the scattering-absorption body B. In the present embodiment, the light incident position I is set at one location of the surface Ba of the scattering-absorption body B. The light incident means 10 comprises a pulsed light source 11 that generates the pulsed light P and a light guide for light incidence 12. An input terminal of the light guide for light incidence 12 is optically connected to the pulsed light source 11. An output terminal of the light guide for light incidence 12 is disposed at the light incident position I of the scattering-absorption body B.

Various devices, for instance a light-emitting diode, a laser diode, and various types of pulsed laser devices, are used as the pulsed light source 11. As the pulsed light P generated in the pulsed light source 11 there is used pulsed light (for instance, near-infrared pulsed light) the time width of the pulses whereof is short enough to enable measurement of the variation amount of an absorption coefficient of the scattering-absorption body B and such that the center wavelength of the pulsed light is a wavelength of high absorptance in the light absorption characteristic of the substance to be measured. For instance, an optical fiber is used as the light guide for light incidence 12.

The light detecting means 20 is means for detecting, as detected light, the pulsed light P that propagates through the interior of the scattering-absorption body B. In the present embodiment, a light detecting position D is set at one location of the surface Ba of the scattering-absorption body B. The light detecting means 20 comprises a light guide for light detection 21 and a light detector 22 that detects light and converts the latter to an electrical detection signal. An input terminal of the light guide for light detection 21 is disposed at the light detecting position D of the scattering-absorption body B. An output terminal of the light guide for light detection 21 is optically connected to the light detector 22.

For instance, an optical fiber is used as the light guide for light detection 21. For instance, a photomultiplier, a photodiode, an avalanche photodiode, a PIN photodiode or the like is used as the light detector 22. The light detector 22 may have a spectral sensitivity characteristic that enables sufficient detection of light intensity at the wavelength range of pulsed light P that exits through the pulsed light source 11. A high-sensitivity and/or high-gain light detector may be used when detected light is weak.

The signal processing means 30 is a means for performing predetermined signal processing on the light detection signal that is provided by the light detecting means 20. The signal processing means 30 of the present embodiment comprises a temporal profile measuring unit 31. The temporal profile measuring unit 31 is electrically connected to the light detector 22. The temporal profile measuring unit 31 acquires a temporal profile of the light intensity of detected light, on the basis of the light detection signal from the light detector 22. In order to acquire the temporal profile, the pulsed light source 11 provides a trigger signal, which denotes the emission timing of the pulsed light P, to the temporal profile measuring unit 31. Incidence and detection of the pulsed light P are performed over a plurality of measurement times, so that a respective temporal profile at each measurement time is obtained as a result.

The calculation means 40 is means for calculating information relating to the amount of substance to be measured in the region to be measured B1 of the scattering-absorption body B, on the basis of the temporal profile obtained by the temporal profile measuring unit 31. The calculation means 40 comprises an arithmetic processing unit 41. The arithmetic processing unit 41 performs a predetermined calculation to calculate thereby a concentration variation amount of the substance to be measured having had the influence of the intervening tissue B2 excluded therefrom. The arithmetic processing unit 41 is electrically connected to the temporal profile measuring unit 31, and receives, from the temporal profile measuring unit 31, information relating to the temporal profile of the detected light.

Figure 2:
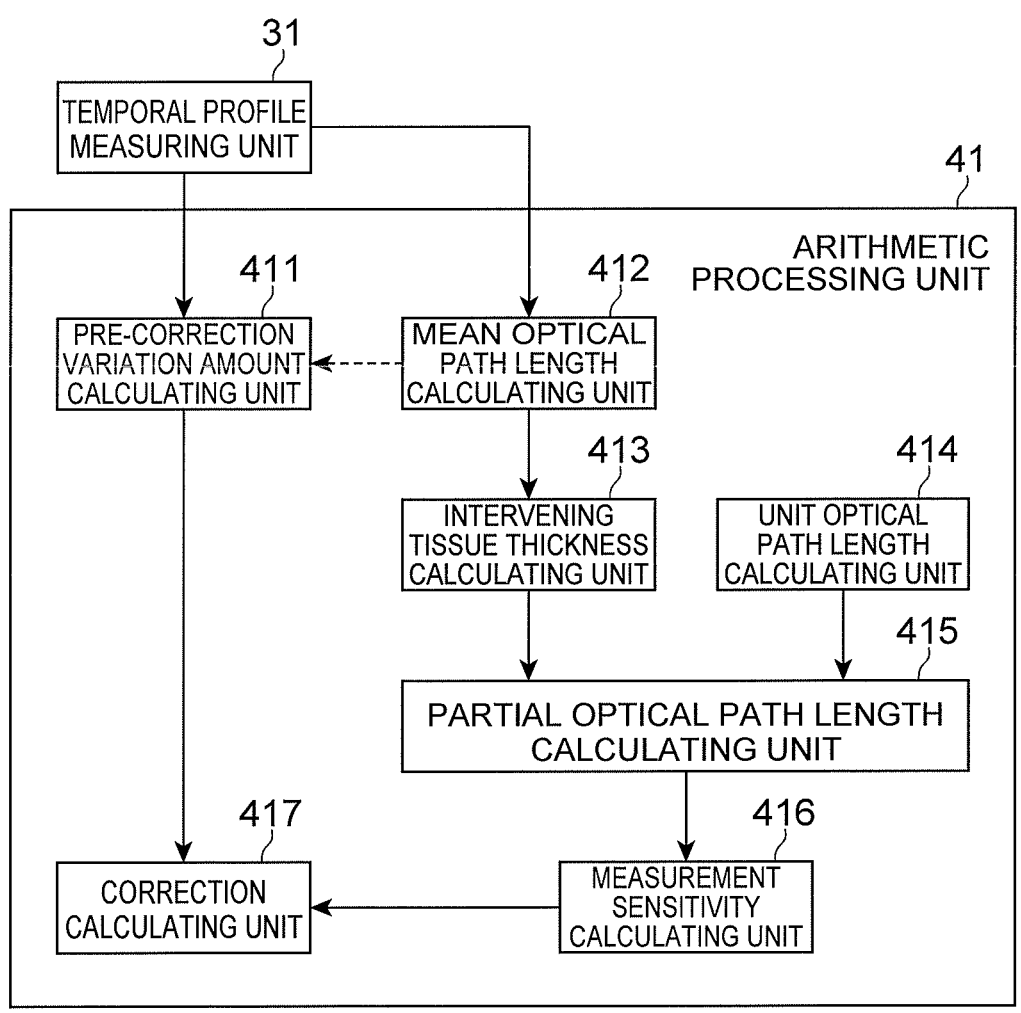
FIG. 2 is a block diagram illustrating an example of the internal configuration of an arithmetic processing unit.

FIG. 2 is a block diagram illustrating an example of the internal configuration of the arithmetic processing unit 41. As illustrated in FIG. 2, the arithmetic processing unit 41 of the present embodiment comprises a pre-correction variation amount calculating unit 411, an mean optical path length calculating unit 412, an intervening tissue thickness calculating unit 413, a unit optical path length calculating unit 414, a partial optical path length calculating unit 415, a measurement sensitivity calculating unit 416 and a correction calculating unit 417.

The pre-correction variation amount calculating unit 411 works out a variation amount of the absorption coefficient $\Delta\mu a$, from a previous measurement time in the scattering-absorption body B, on the basis of the temporal profile of the detected light as provided by the temporal profile measuring unit 31. The variation amount of the absorption coefficient $\Delta\mu a$ may be calculated from changes in the light intensity of detected light, or may be calculated in the form of the difference of a quantitative value $\mu a$ that is obtained according to a diffusion equation. The concentration variation amount of the substance to be measured (oxyhemoglobin, deoxyhemoglobin and total hemoglobin) can be derived from the $\Delta\mu a$ calculated by the pre-correction variation amount calculating unit 411.

The mean optical path length calculating unit 412 calculates an mean optical path length L on the basis of the temporal profile of the detected light as provided by the temporal profile measuring unit 31. The mean optical path length L may be provided to the pre-correction variation amount calculating unit 411, for the purpose of analysis.

The intervening tissue thickness calculating unit 413 receives information relating to the mean optical path length L from the mean optical path length calculating unit 412, and estimates the thickness of the intervening tissue B2 (dimension A illustrated in FIG. 1) on the basis of a correlation between the mean optical path length L and the thickness of the intervening tissue B2. The correlation between the mean optical path length L and the thickness A of the intervening tissue B2 is stored beforehand in a storage means, for instance a nonvolatile memory. The intervening tissue thickness calculating unit 413 reads a numerical value relating to the thickness A that corresponds to the mean optical path length L from the storage means.

The unit optical path length calculating unit 414 calculates an optical path length LA per unit thickness of the intervening tissue B2. In the unit optical path length calculating unit 414, information relating to the correlation between the thickness A of the intervening tissue B2 and a pre-correction variation amount $\Delta X$ in a case where there is varied only the concentration of the substance to be measured, is stored beforehand in a storage means, for instance a nonvolatile memory. The thickness A of the intervening tissue B2 may be estimated out of the storage means of the intervening tissue thickness calculating unit 413, or may be measured externally to the device, for instance by way of an ultrasonic device. The unit optical path length calculating unit 414 calculates the optical path length LA per unit thickness of the intervening tissue B2 on the basis of the abovementioned correlations.

For instance, the unit optical path length calculating unit 414 estimates optical path length LA per unit thickness of the intervening tissue B2, in the below-described manner, from a correlation between the thickness A of the intervening tissue B2 and the pre-correction variation amount $\Delta X$ in a case where there is varied only the concentration of the substance to be measured.

Firstly, the numerical value worked out on the basis of Expression (1) can be regarded as a measurement sensitivity (correction coefficient S). In Expression (1), LM is the optical path length of a portion of passage through the region to be measured B1, from within the mean optical path length L of passage through the entire scattering-absorption body B, and LF is the optical path length of the portion of passage through the intervening tissue B2.

[Expression 1]

$$S = LM/L = (L-LF)/L \qquad (1)$$

The partial optical path length LF of passage through the intervening tissue B2 is represented, for instance, by Expression (2).

[Expression 2]

$$LF = 2 \times A \times LA \qquad (2)$$

Herein, A is the thickness of the intervening tissue B2 as provided by the intervening tissue thickness calculating unit 413, and LA is the optical path length per unit thickness of the intervening tissue B2.

Expression (3) represents relationships between the optical path length LA per unit thickness of the intervening tissue B2, a variation amount of the substance to be measured $\Delta X_{B1}$ at a region to be measured in a case where there is varied only the concentration of the substance to be measured, and the pre-correction variation amount $\Delta X$ obtained by measurement in a case where there is varied only the substance to be measured.

[Expression 3]

$$\Delta X = (LM/L) \times \Delta X_{B1}$$
$$= ((L-LF)/L) \times \Delta X_{B1}$$
$$= ((L-(2 \times A \times LA)/L) \times \Delta X_{B1} \quad (3)$$

The following processing is performed next based on the assumption that there are virtually no individual differences in the oxygen consumption amount at one same site of the region to be measured B1. The above Expression (3) relating to a plurality of individuals is prepared by using the mean optical path length L, at rest, acquired as a result of light incidence at one location and light detection at one location, the intervening tissue thickness A estimated from the mean optical path length L, and the pre-correction variation amount $\Delta X$ of the substance to be measured upon change of only the substance to be measured. The unit optical path length calculating unit 414 calculates a shared LA (optical path length per unit thickness of the intervening tissue B2) and $\Delta X_{B1}$ (variation amount of the substance to be measured in the region to be measured B1), in such a manner that Expression (4), derived from Expression (3), is minimized.

[Expression 4]

$$\sum \left\{ \Delta X - \left( L - \frac{2 \times A \times LA}{L} \right) \times \Delta X_{B1} \right\}^2 \quad (4)$$

If information relating to the correlation between the thickness A of the intervening tissue B2 and the pre-correction variation amount $\Delta X$ in a case where there is varied only the concentration of the substance to be measured, is stored in the storage means, and the optical path length LA per unit thickness of the intervening tissue B2 is defined, a separate measurement in which only the concentration of the substance to be measured is caused to vary need not be performed, for each test subject.

The partial optical path length calculating unit 415 calculates the optical path length of the portion of passage through the intervening tissue B2 (partial optical path length LF), within the mean optical path length L of passage through the entirety of the scattering-absorption body B. The partial optical path length calculating unit 415 works out the partial optical path length LF from the thickness A of the intervening tissue B2 as provided by the intervening tissue thickness calculating unit 413, and the optical path length LA per unit thickness of the intervening tissue B2 as provided by the unit optical path length calculating unit 414, using for instance Expression (2).

The measurement sensitivity calculating unit 416 calculates a measurement sensitivity (correction coefficient) S estimated according to Expression (1), on the basis of the partial optical path length LF.

The correction calculating unit 417 uses the measurement sensitivity S calculated by the measurement sensitivity calculating unit 416 to correct the variation amount of the substance to be measured (oxyhemoglobin, deoxyhemoglobin and total hemoglobin), as calculated by the pre-correction variation amount calculating unit 411.

Returning to FIG. 1, the display unit 70 is connected to the main body 60. The display unit 70 displays, as the case may require, the thickness A of the intervening tissue B2 as well as variation amount of substance to be measured (oxyhemoglobin, deoxyhemoglobin and total hemoglobin) after correction.

Figure 3:
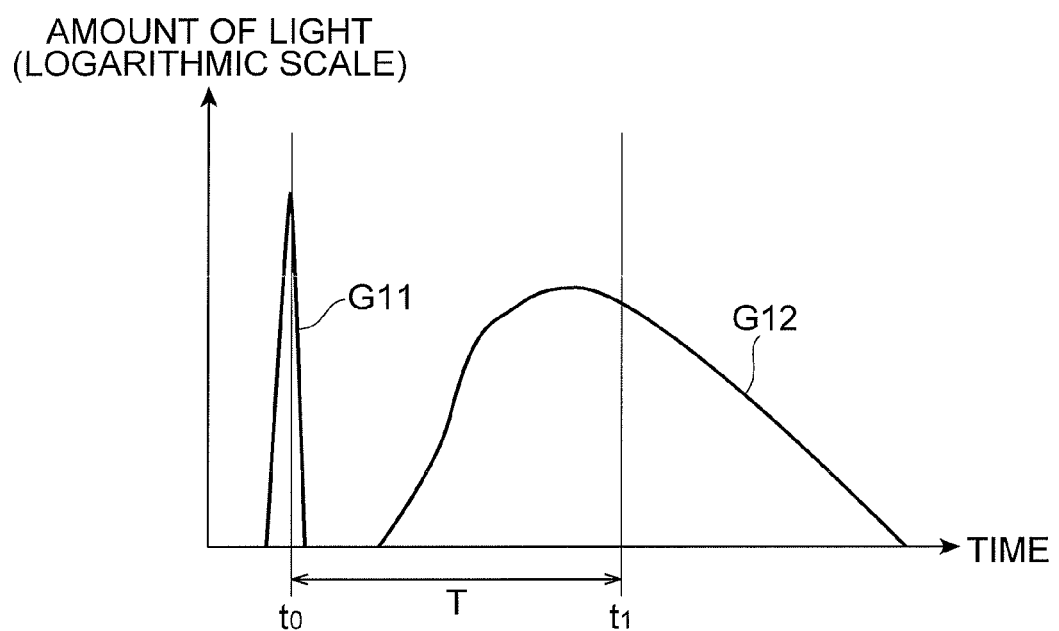
FIG. 3 is a diagram for explaining a calculation method of an mean optical path length in an mean optical path length calculating unit.

A detailed explanation follows next on a method for measuring a scattering-absorption body that utilizes the above-described device for measuring a scattering-absorption body 1. FIG. 3 is a diagram for explaining a calculation method of the mean optical path length L in the mean optical path length calculating unit 412. In FIG. 3, the ordinate axis represents amount of light (logarithmic scale), and the abscissa axis represents time. Graph G11 is a temporal profile (incidence temporal profile) of the intensity of the pulsed light that irradiates the scattering-absorption body B, from the light incident means 10, at time $t_0$. Graph G12 is a temporal profile (detected temporal profile) of detected light intensity corresponding to pulsed light that is incident at time $t_0$. The time that it takes for light that propagates through the interior of the scattering-absorption body B to reach the light detecting position D is non-uniform, and depends on the propagation conditions. Moreover, the light is attenuated on account of scattering and absorption by the scattering-absorption body B. Therefore, the detected temporal profile exhibits a certain distribution curve as shown in the graph G12 in FIG. 3. The mean optical path length L (T×c) can be calculated by multiplying an mean propagation time T, from time $t_0$ until time $t_1$, which is calculated as the centroid of the detected temporal profile, by the speed of light c. In this calculation, the point in time of the centroid of the incidence temporal profile may be used as time $t_0$.

Figure 4:
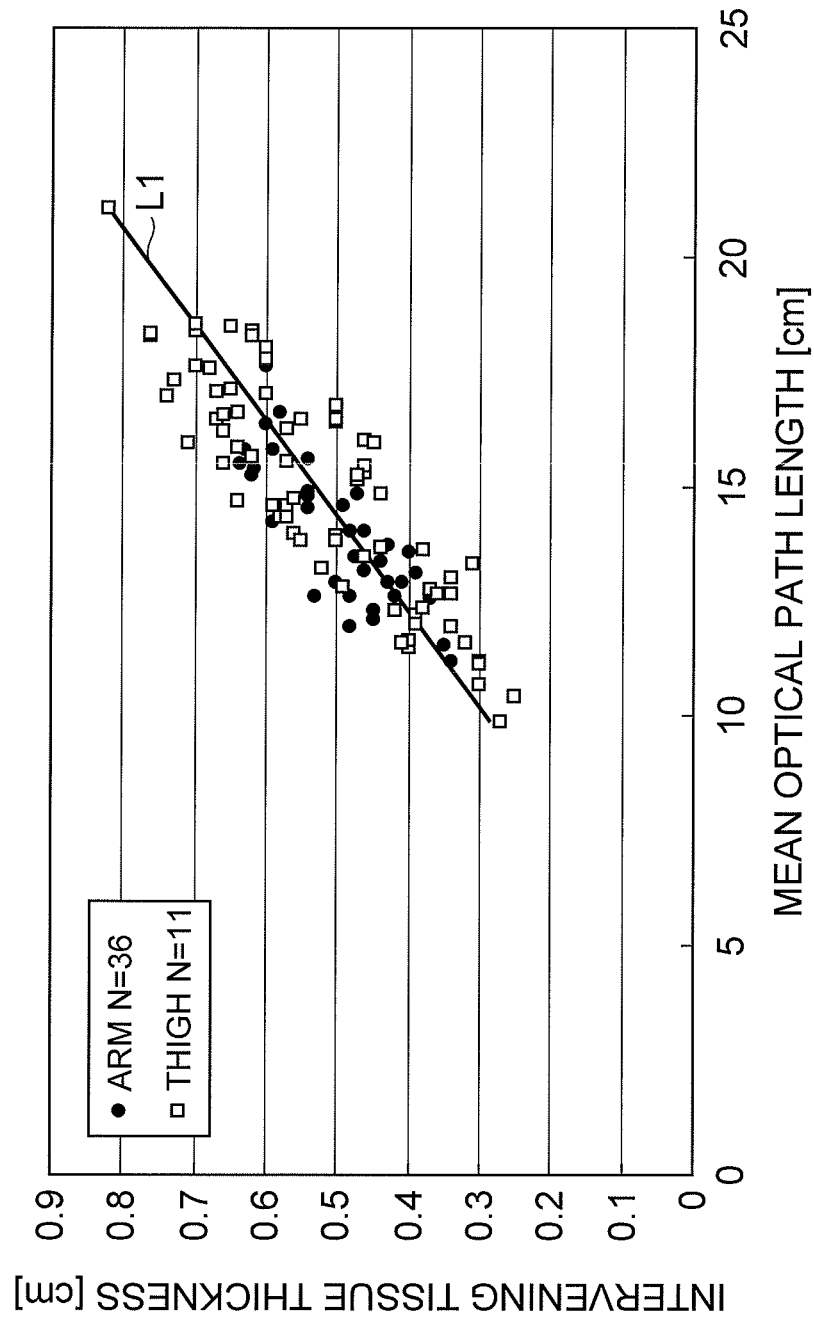
FIG. 4 is a graph that plots a relationship between an mean optical path length actually measured using the method for measuring a scattering-absorption body and the thickness of intervening tissue (fat) measured using an ultrasonic device.

FIG. 4 is a graph that plots the relationship between the mean optical path length L actually measured in accordance with such a method, and the thickness A of the intervening tissue (fat) B2 as measured using an ultrasonic device. In FIG. 4, the ordinate axis represents the intervening tissue thickness A (cm), and the abscissa axis represents the mean optical path length L (cm). In FIG. 4, the black-circle plots denote an instance where the scattering-absorption body B is the forearm (N=36, where N is the number of subjects), and the square plots denote an instance where the scattering-absorption body B is the thigh (N=11, with the thigh being measured at a plurality of places).

As FIG. 4 shows, the thicker the intervening tissue thickness A, the longer the mean optical path length L is. The correlation between the intervening tissue thickness A and the mean optical path length L can be appropriately represented, for instance, by the approximate straight line L1 illustrated in FIG. 4. The approximate straight line L1 is represented by Expression (5), where the $R^2$ value was 0.7391. The relational expression is not limited to Expression (5), and the approximate expression may vary as a result of an increase in the number of data points.

[Expression 5]

$$A = 0.0505L - 0.2221 \quad (5)$$

The thickness A of the intervening tissue B2 can be estimated from the mean optical path length L on the basis of the above-mentioned relational Expression (5). In the present embodiment, the thickness A of the intervening tissue B2 is estimated, by the intervening tissue thickness calculating unit 413, by using Expression (5) and the mean optical path length L that is obtained by the mean optical path length calculating unit 412. In a conventional CW measurement the mean optical path length cannot be measured, and there is used a constant value (differential path length factor; DPF) for the distance between optical fibers.

Accordingly, there are no individual differences in mean optical path length, and the mean optical path length can be treated only with normalized values.

Figure 5:
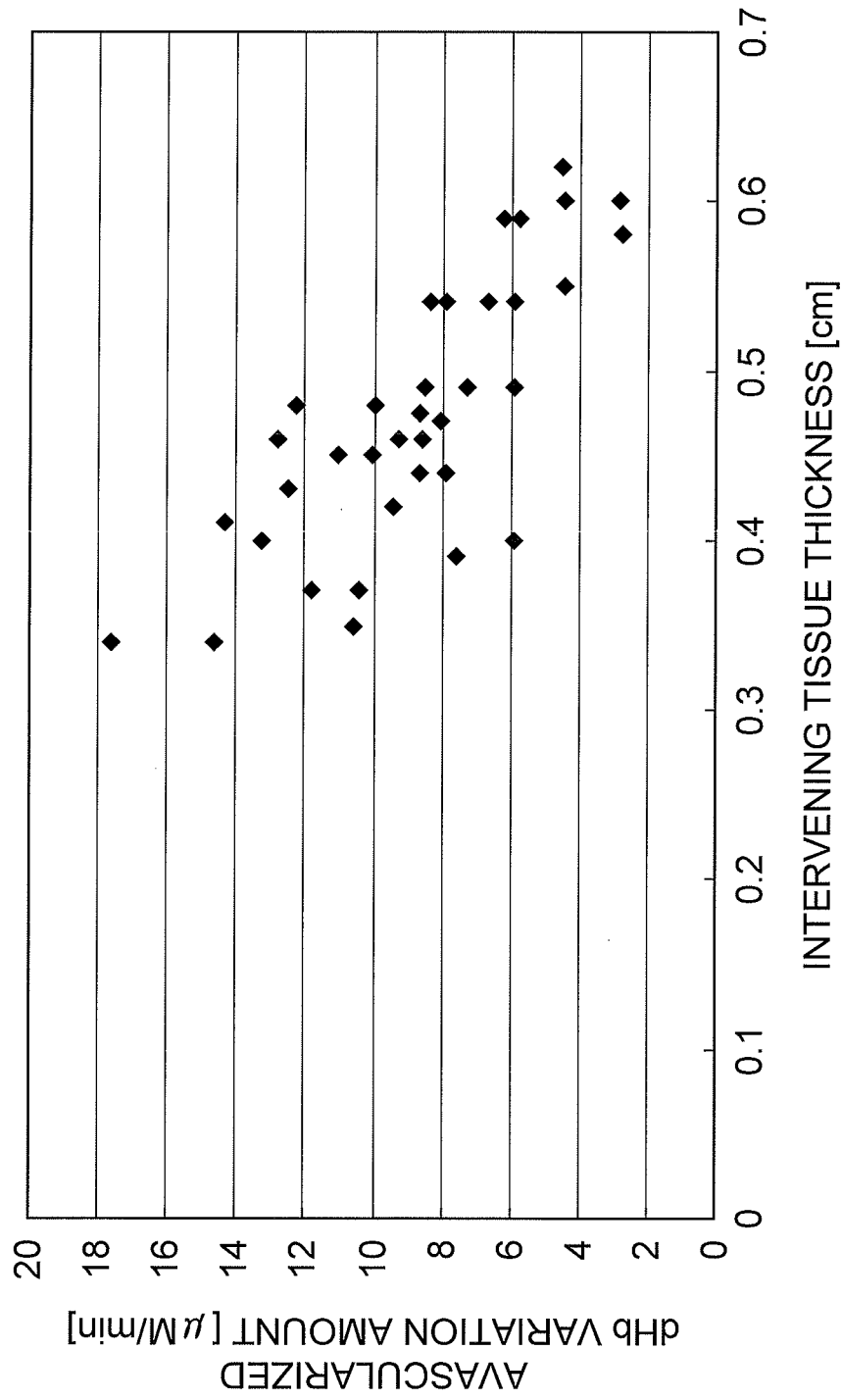
FIG. 5 is a graph that plots results of a measurement of the variation amount, per minute, of amount of substance to be measured (deoxyhemoglobin amount), and a relationship with respect to intervening tissue thickness, in a case of arterial avascularization, at 250 mmHg, of the forearm.
Figure 6:
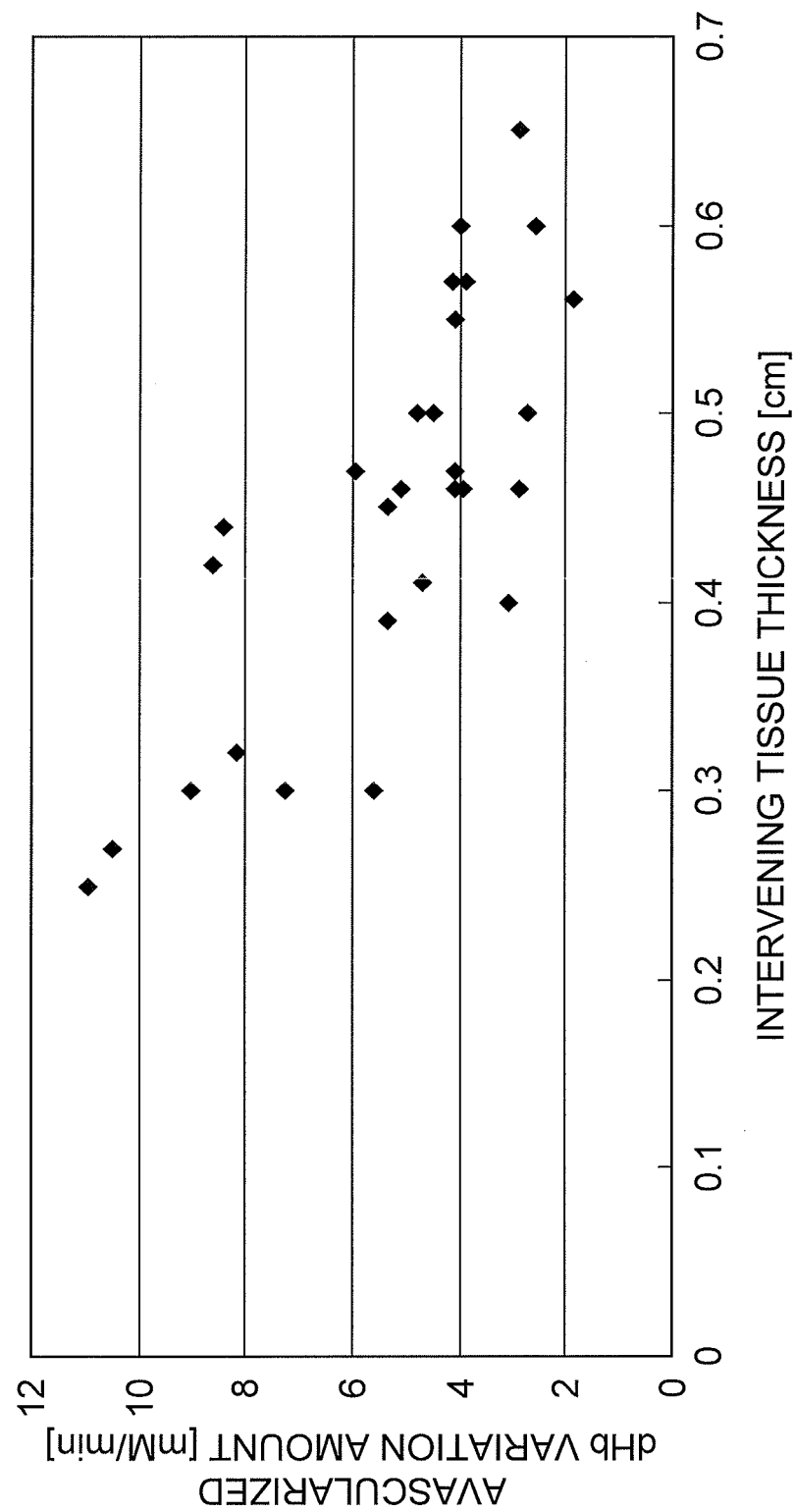
FIG. 6 is a graph that plots results of a measurement of the variation amount, per minute, of amount of substance to be measured (deoxyhemoglobin amount), and a relationship with respect to intervening tissue thickness, in a case of arterial avascularization, at 250 mmHg, of the thigh.

FIG. 5 and FIG. 6 are graphs in which there are respectively plotted the results of a measurement of the variation amount, per minute, of the amount of substance to be measured (deoxyhemoglobin amount), and a relationship with respect to the intervening tissue thickness A, in a case of arterial avascularization, at 250 mmHg, for the forearm (N=36) and the thigh (N=7). In FIG. 5 and FIG. 6, the ordinate axis represents the variation of deoxyhemoglobin amount, and the abscissa axis represents the intervening tissue thickness A.

In an avascularized state, i.e. a state of no blood outflow or inflow, oxyhemoglobin decreases and deoxyhemoglobin increases on account of oxygen consumption by muscle. As FIG. 5 and FIG. 6 illustrate, the thicker the intervening tissue thickness A, the smaller is the measured value of the variation of the deoxyhemoglobin amount. Individual differences in the muscle oxygen consumption amount, at a same site in the scattering-absorption body B, are small. Therefore, this indicates that the greater the intervening tissue thickness A is, the greater is the underestimation of the measured value of the deoxyhemoglobin amount. In the above-described device for measuring a scattering-absorption body 1, the correction calculating unit 417 corrects this underestimation using the measurement sensitivity S that is given by Expression (1).

The measurement sensitivity calculating unit 416 can work out the measurement sensitivity S on the basis of Expression (1) if, when working out the measurement sensitivity S, it is possible to estimate a partial optical path length LM, of the region to be measured B1, in the mean optical path length L. However, when relying on a simulation, although the partial optical path length LM can be estimated, the optical coefficients and thickness of the various constituent elements (region to be measured B1, intervening tissue B2 and so forth) have then to be assumed, which is not realistic. In the present embodiment, by contrast, the intervening tissue thickness A can be estimated from the mean optical path length L, and hence the unit optical path length calculating unit 414 can work out the optical path length LA per unit thickness of the intervening tissue B2 from measurement data by light incidence at one location and light detection at one location, and from the relationship between the variation amount of the substance to be measured and the mean optical path length L. The measurement sensitivity calculating unit 416 can further work out the partial optical path lengths LM and LF, as well as the measurement sensitivity S, from Expressions (1) and (2), by using the obtained optical path length LA per unit thickness of the intervening tissue B2, the mean optical path length L, and the intervening tissue thickness A.

In a case where, for instance, the region to be measured B1 is muscle and the intervening tissue B2 is fat, the amount of blood as well as oxygen consumption amount in fat are much smaller than in muscle. Accordingly, it is deemed that virtually no change in the amount of blood in the intervening tissue B2 occurs during avascularization. By contrast, the oxygen consumption amount in the region to be measured B1 is large. Accordingly, the relationship between a deoxyhemoglobin variation amount $\Delta Hbm$ in the region to be measured B1, which increases through avascularization, and a deoxyhemoglobin variation amount $\Delta Hb$ obtained by measurement, is represented by Expression (6).

[Expression 6]

$$\Delta Hb = (LM/L) \times \Delta Hbm \quad (6)$$
$$= ((L - LF)/L) \times \Delta Hbm$$
$$= ((L - (2 \times A \times LA))/L) \times \Delta Hbm$$

Based on the assumption that there are virtually no individual differences in the oxygen consumption amount at a same site in the region to be measured B1, Expression (6) above relating to a plurality of individuals is prepared by using the mean optical path length L at rest, as acquired through detection of light incidence at one location and light detection at one location, the intervening tissue thickness A estimated from the mean optical path length L, and the deoxyhemoglobin variation amount $\Delta Hb$ during avascularization. The unit optical path length calculating unit 414 calculates a shared LA (optical path length per unit thickness of the intervening tissue B2) and $\Delta Hbm$ (deoxyhemoglobin variation amount in the region to be measured B1) such that Expression (7), which is derived from Expression (6), is minimized. The measurement sensitivity calculating unit 416 can work out, as a result, the measurement sensitivity S for each test subject, on the basis of Expressions (1) and (2), by using the obtained optical path length LA per unit thickness of the intervening tissue B2, the mean optical path length L and the intervening tissue thickness A.

[Expression 7]

$$\sum \left\{ \Delta Hb - \left(L - \frac{2 \times A \times LA}{L}\right) \times \Delta Hbm \right\}^2 \quad (7)$$

In the method of the present embodiment, the burden of avascularization or the like need not be imposed on the test subject if the relationship between the measurement sensitivity S and the intervening tissue thickness A or mean optical path length L can be derived from data stored beforehand, since in such cases it suffices to use the relational expression.

In actuality, LF and $\Delta Hbm$ in the forearm and thigh were worked out from the measurement data of FIG. 5 and FIG. 6. Herein, $\Delta Hbm$ was estimated at 23.11 μM for the forearm and at 13.47 μM for the thigh. The partial optical path length LF with respect to 1 cm of intervening tissue thickness (fat thickness), was estimated at 9.14 cm for the forearm and at 9.57 cm for the thigh.

Figure 7:
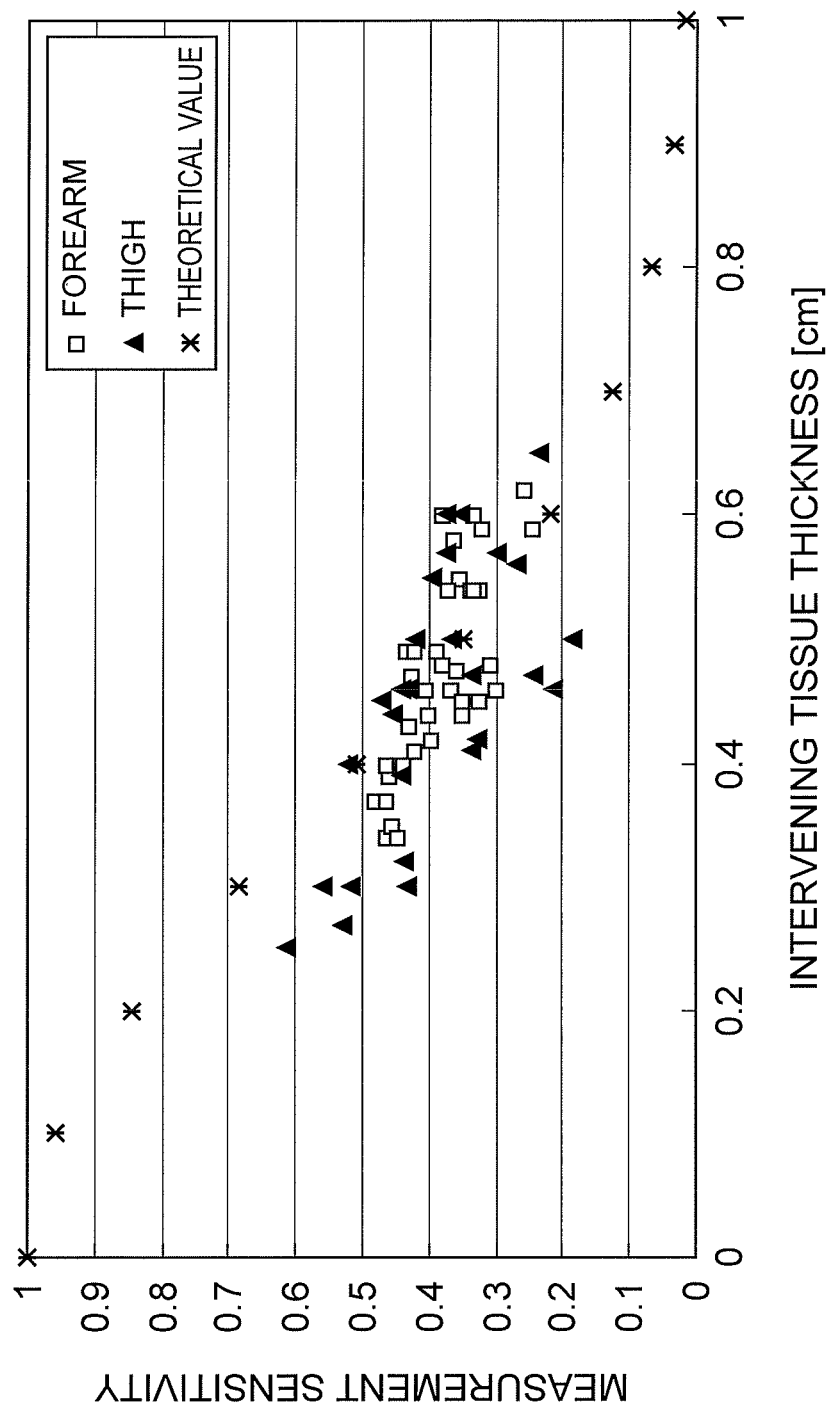
FIG. 7 is a graph that plots a relationship between mean optical path length actually measured and measurement sensitivity obtained from Expression (1)

FIG. 7 is a graph that plots a relationship between the mean optical path length L actually measured and the measurement sensitivity S obtained from Expression (1). In FIG. 7, the ordinate axis represents the measurement sensitivity S and the abscissa axis represents the intervening tissue thickness A. In FIG. 7, the square plots represent the forearm, the triangular plots the thigh, and the asterisk-like plots represent theoretical values. The theoretical values are given by the expression below.

[Expression 8]

$$S = \exp\left\{-\left(\frac{A}{0.469}\right)^2\right\} \quad (8)$$

As illustrated in FIG. 7, the thicker the intervening tissue thickness A, the smaller the measurement sensitivity S is. The measurement sensitivity S can be derived from the mean optical path length L, even without measuring the intervening tissue thickness A, by replacing the intervening tissue thickness A by the mean optical path length L in the abscissa axis of FIG. 7, using Expression (5) above. The measurement sensitivity calculating unit 416 illustrated in FIG. 2 calculates the measurement sensitivity S that is used in the measurement, from the relational expression between the measurement sensitivity S and the intervening tissue thickness A.

Lastly, the correction calculating unit 417 divides the measured value (for instance, deoxyhemoglobin variation amount ΔHb) relating to the amount of substance to be measured, by the measurement sensitivity S. The value of the region to be measured B1 (for instance, deoxyhemoglobin variation amount ΔHbm of the region to be measured B1), excluding the influence of the intervening tissue B2, can estimated as a result.

The partial optical path length LA per unit length (1 cm) of the intervening tissue B2 was estimated to be, for instance, about 9.4 cm in average, according to the above method. In consequence, the partial optical path length LF of the intervening tissue B2 can be calculated by measuring the mean optical path length L, estimating the intervening tissue thickness A on the basis of the mean optical path length L, and plugging the foregoing into Expression (2) together with the estimated numerical value of the partial optical path length LA. Herein, the contribution rate of the interior of the region to be measured B1 can be estimated by Expression (1) with using the partial optical path length LF, and the measurement sensitivity S can be worked out.

Figure 8:
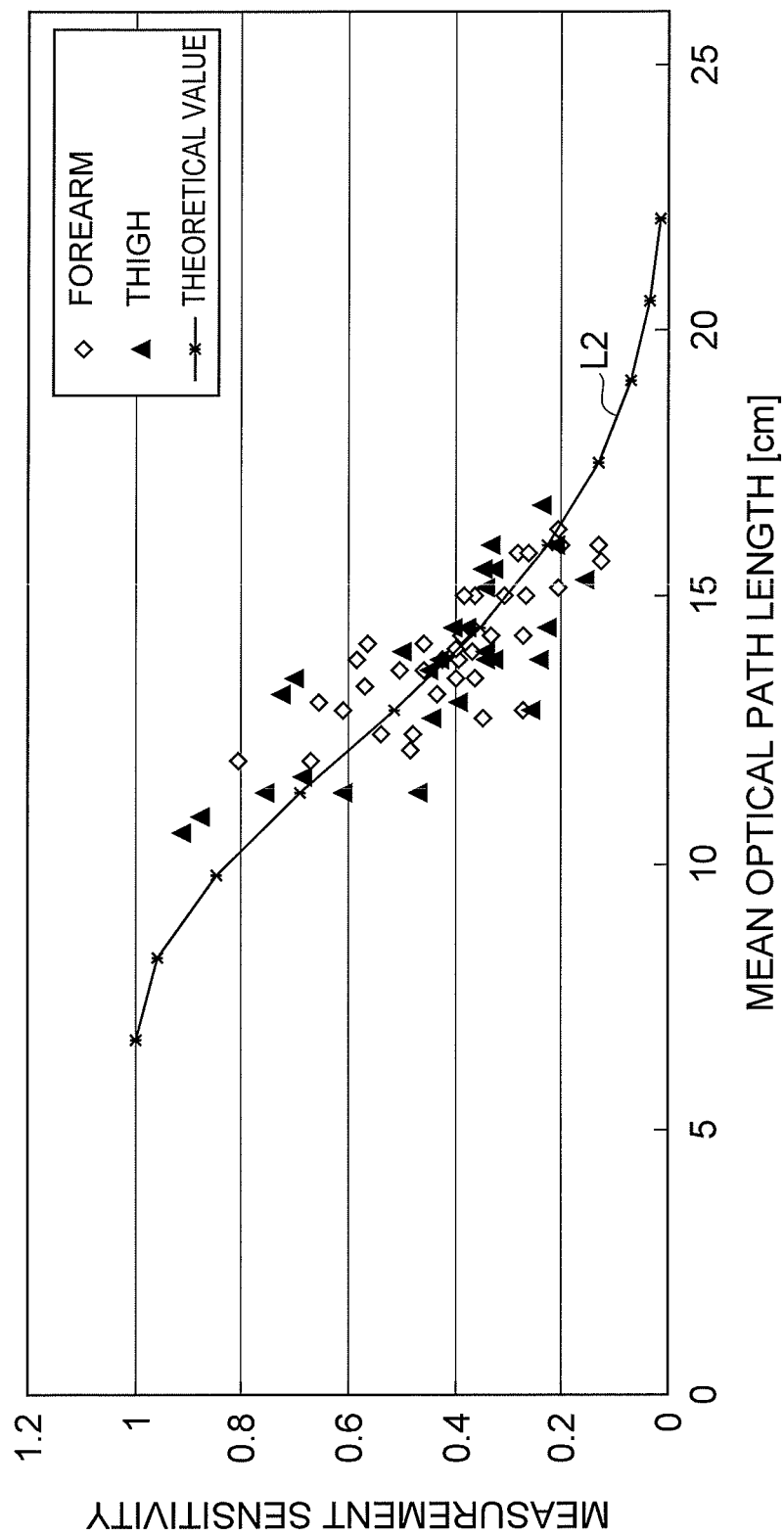
FIG. 8 is a graph illustrating a correlation between mean optical path length and measurement sensitivity.

Converting the abscissa axis of FIG. 7 to the mean optical path length L yields a graph such as the one illustrated in FIG. 8. FIG. 8 illustrates a correlation between the mean optical path length L and the measurement sensitivity S, and shows that the longer the mean optical path length L is, the smaller the measurement sensitivity S becomes. That is, the measurement sensitivity S can be derived if the mean optical path length L at rest is measured, and hence there is no need to measure the intervening tissue thickness A using a method such as ultrasonic measurement or the like. FIG. 8 depicts also a theoretical curve L2 for which the measurement sensitivity S is 1 when the intervening tissue thickness A is zero. Expression (9) gives the function of the theoretical curve L2. The relational expression used for estimating the measurement sensitivity S is not limited to this theoretical curve L2, and an optimal approximate expression may be used.

[Expression 9]

$$S = \exp\left\{-\left(\frac{0.0505 \times L - 0.2221}{0.491}\right)^2\right\} \quad (9)$$

An explanation follows next on the results (for N=14) obtained by measurement using a time-resolved spectroscopy system (TRS), and by plethysmographic measurement performed simultaneously therewith, in order to check whether the correction of the measured value by the above-described mean optical path length L is appropriate or not. Herein, plethysmography involves venous avascularization of the measurement site (for instance, the forearm), and measurement, in accordance with various methods, of the volume of the site that increases through continued arterial perfusion. In TRS, the variation amount of the substance to be measured (for instance, for instance hemoglobin) per unit time upon venous avascularization of the measurement site can be regarded as the blood flow. Therefore, the thickness A of the intervening tissue (fat) and the measurement sensitivity S were estimated in accordance with the above-described method, on the basis of the mean optical path length L measured by TRS, the TRS measured value (blood flow) was corrected using the measurement sensitivity S, and the correction value and the measured value by plethysmography were compared.

Firstly, a protocol involved three sets of forearm venous avascularization (40 mmHg) for 10 seconds, and avascularization releasing for 10 seconds. The blood flow at that time was taken as the blood flow at rest (i.e. initial value). This was followed next by 3 minutes of arteriovenous avascularization (250 mmHg). The 3-minute avascularization was then released, and, thereafter, there followed several repeats of venous avascularization (40 mmHg) for 10 seconds and avascularization releasing for 10 seconds. In the reaction after arteriovenous avascularization for 3 minutes, which is referred to as reactive hyperemia, the blood flow after resumption of perfusion increases several-fold with respect to the blood flow at rest prior to avascularization. Various blood flow data items within one body can be accordingly acquired.

Figure 9:
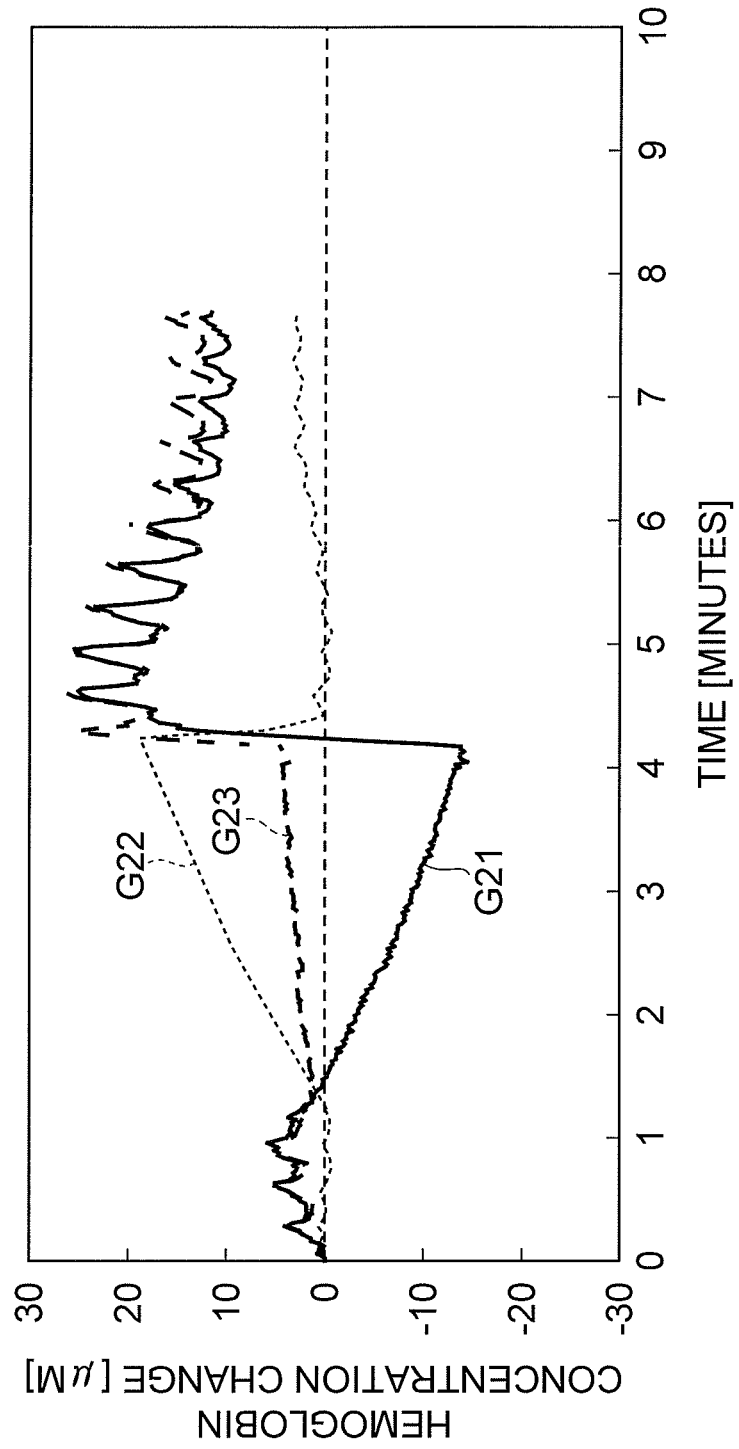
FIG. 9 is a graph illustrating a typical example of TRS measurement results (perfusion variation amount)

FIG. 9 is a graph illustrating a typical example of TRS measurement results (perfusion variation amount) when the above protocol is carried out in practice. In FIG. 9, the ordinate axis represents the variation amount (μM) of hemoglobin concentration, and the abscissa axis represents time (minutes). In the figure, graph G21 represents the amount of oxyhemoglobin (HbO$_2$), graph G22 represents the amount of deoxyhemoglobin (Hb), and graph G23 represents the total hemoglobin amount (tHb).

FIG. 10 is a chart illustrating the mean optical path length L, the intervening tissue thickness A estimated from the mean optical path length L, and the measurement sensitivity S estimated from the partial optical path length LF, for 14 individuals. The blood flow measured value by TRS before correction was divided by the measurement sensitivity S illustrated in FIG. 10, to work out thereby the blood flow measured value after correction.

Figure 11:
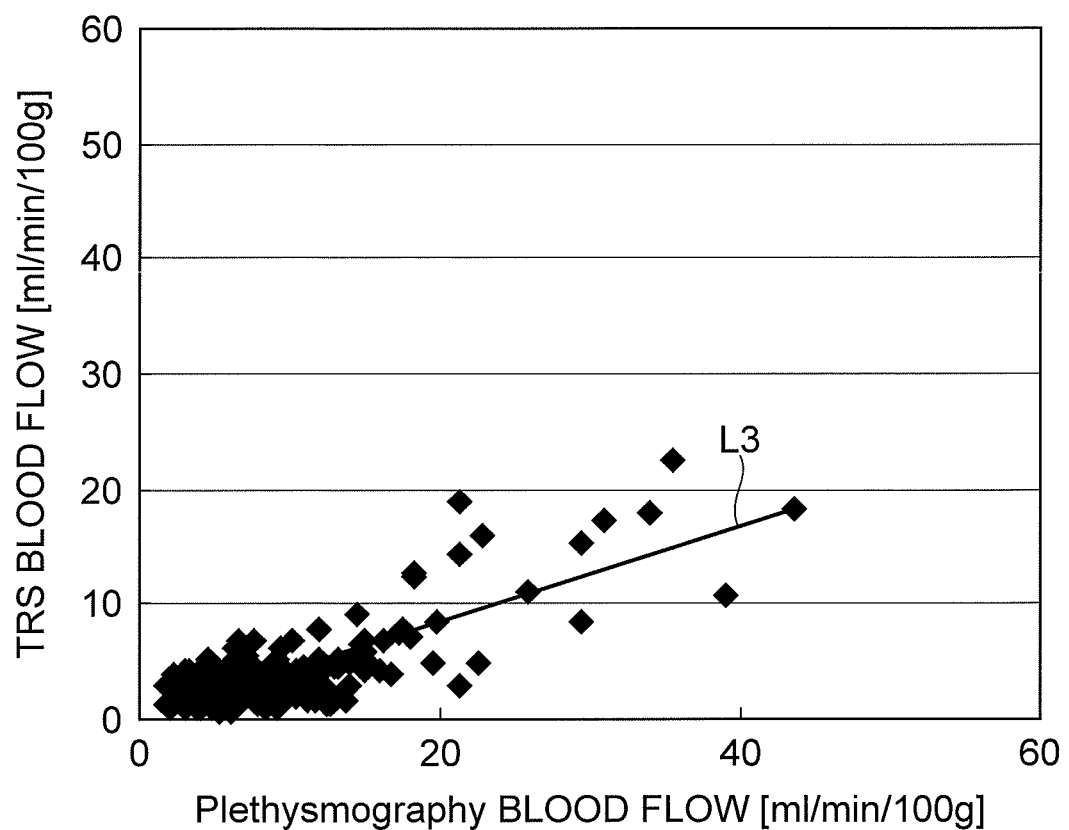
FIG. 11 is a graph that plots a correlation between blood flow measured values pre-corrected by TRS and blood flow measured values by plethysmography.
Figure 12:
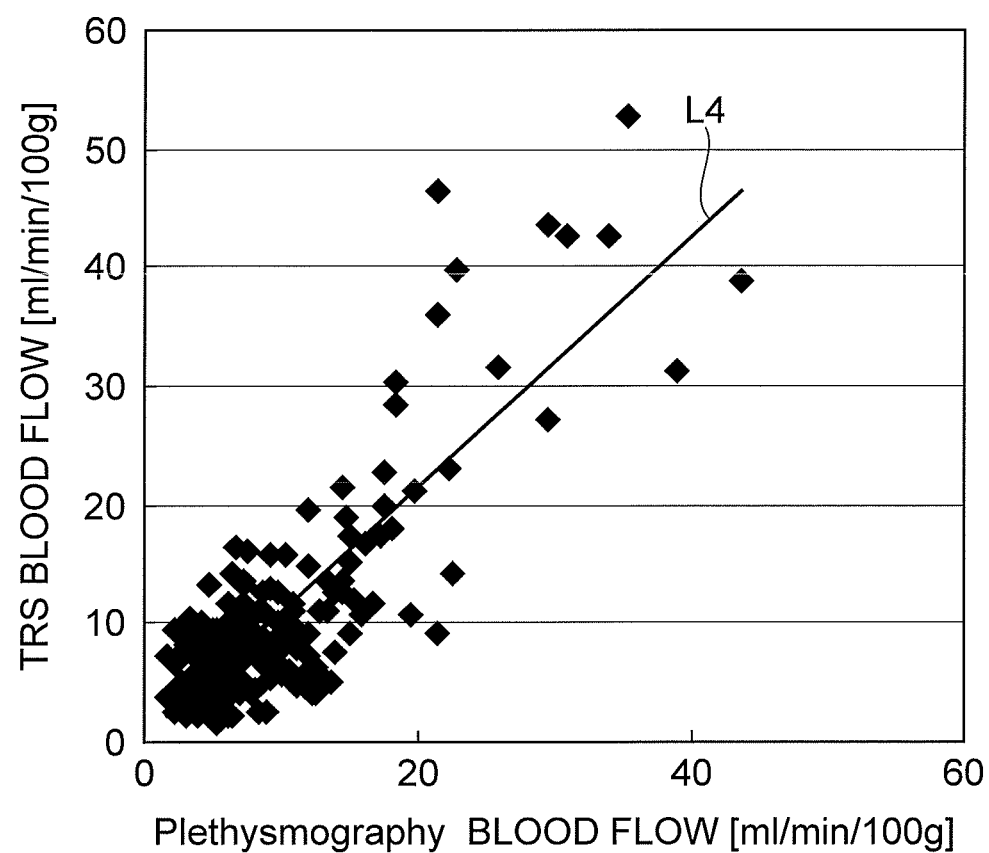
FIG. 12 is a graph that plots a correlation between blood flow measured values measured by TRS and corrected by a measurement sensitivity S, and blood flow measured values by plethysmography.

FIG. 11 and FIG. 12 are graphs in which there is plotted a correlation between blood flow measured values by TRS and blood flow measured values by plethysmography. FIG. 11 illustrates the correlation before correction, and FIG. 12 illustrates the correlations upon correction by the measurement sensitivity S. In FIG. 11 and FIG. 12, the ordinate axis represents blood flow measured values by TRS, and the abscissa axis represents blood flow measured values by plethysmography. The units of blood flow are converted to (ml/min/100 g) in accordance with plethysmography.

As FIG. 11 shows, the slope of the TRS value with respect to the plethysmography value of the approximate straight line L3, before correction, was 0.4. By contrast, as FIG. 12 shows, the slope of the approximate straight line L4 after correction by measurement sensitivity S was substantially 1, and the TRS value was closer to the plethysmography value.

The above indicates that sensitivity of data relating to the amount of substance to be measured can be corrected by just measuring the mean optical path length L, once a correlation is obtained between the measurement sensitivity S and the intervening tissue thickness A or the mean optical path length L.

An example of the above-described method has been described that involved measurement of the blood flow. In measurements relating to muscle metabolism during exercise, a measurement is performed firstly for a resting state, to calculate the measurement sensitivity S and intervening tissue thickness A from the mean optical path length L; thereupon, the blood variation amount during ensuing exercise is corrected by the measurement sensitivity S, to yield a value that is displayed on the display unit 70. As a result, the subject can check the blood variation amount in muscle (with the influence of fat excluded therefrom), and can learn the thickness of fat, in real time.

Figure 13:
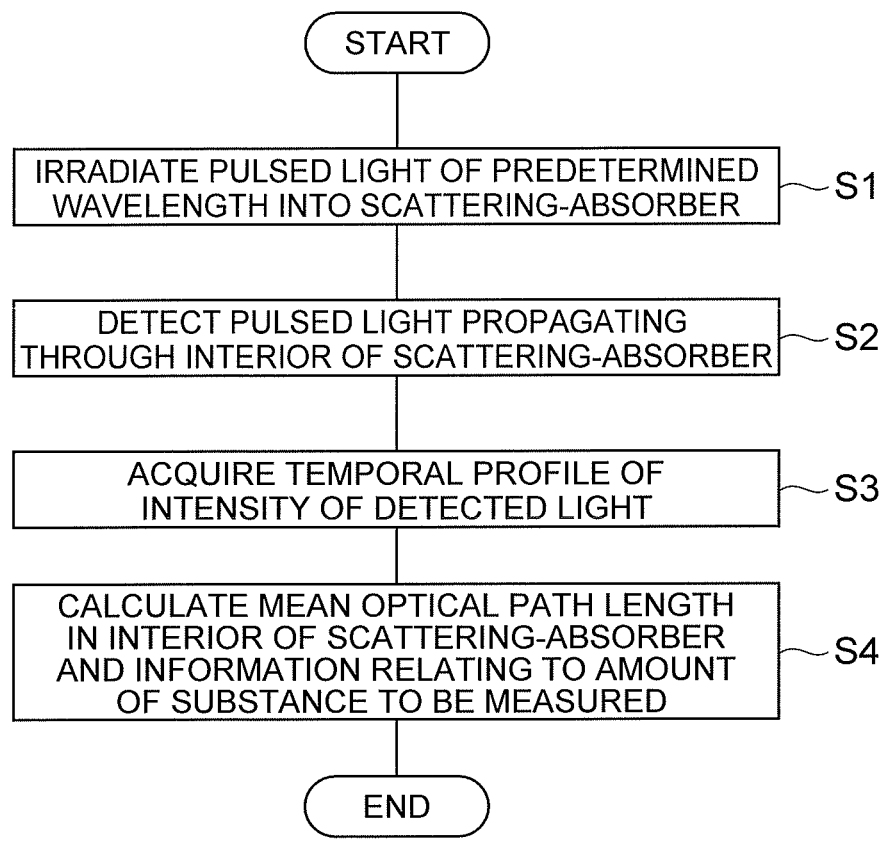
FIG. 13 is a flowchart illustrating the flow of processing in the method for measuring a scattering-absorption body.

FIG. 13 is a flowchart illustrating the flow of processing in the method for measuring a scattering-absorption body described above. In the method for measuring a scattering-absorption body of the present embodiment, firstly, pulsed light P of a predetermined wavelength is caused to be incident, at one light incident position I set on the surface Ba of the scattering-absorption body B, as illustrated in FIG. 1 (light incidence step S1). Next, a light detection signal is obtained by detecting the pulsed light P, which propagates through the interior of the scattering-absorption body B, at one light detecting position D that is set on the surface Ba of the scattering-absorption body B (light detection step S2).

Next, there is acquired a temporal profile of the light intensity of the detected light, on the basis of the light detection signal (signal processing step S3). The mean optical path length L in the interior of the scattering-absorption body B as well as information (variation amount and so forth) relating to the amount of substance to be measured in the region to be measured B1 are calculated on the basis of the temporal profile (calculation step S4). In the calculation step S4, information relating to the amount of substance to be measured is corrected, on the basis of the mean optical path length L, such that the longer the mean optical path length L, the greater is the amount of substance to be measured. For instance, the longer the mean optical path length L, the greater is the intervening tissue thickness A (FIG. 4). Hence, the information relating to the amount of substance to be measured may be corrected on the basis of such a correlation acquired beforehand. Alternatively, the longer the mean optical path length L, the smaller is the measurement sensitivity S (FIG. 8). Hence, the information relating to the amount of substance to be measured may be corrected on the basis of such a correlation acquired beforehand. Alternatively, the information relating to the amount of substance to be measured may be corrected on the basis of the optical path length LA per unit thickness of the intervening tissue B2, acquired beforehand. The optical path length LA per unit thickness of the intervening tissue B2 is obtained from the relationship between the variation amount of the substance to be measured and the thickness of the intervening tissue B2 at a time where there is varied only the substance to be measured.

Alternatively, the information relating to the amount of substance to be measured may be corrected on the basis of the correlation, acquired beforehand, between the mean optical path length L and the measurement sensitivity S. In this case, the correlation between the mean optical path length L and the measurement sensitivity S is worked out from the mean optical path length L and the optical path length (partial optical path length LM or LF) of the portion, of the mean optical path length L of passage through the intervening tissue B2 or the region to be measured B1 in the interior of the scattering-absorption body B.

Alternatively, the partial optical path length LF in the intervening tissue B2 within the mean optical path length L in the interior of the scattering-absorption body B may be estimated on the basis of the optical path length LA per unit thickness of the intervening tissue B2, and the intervening tissue thickness A obtained from a correlation, acquired beforehand, between the mean optical path length L and the intervening tissue thickness A; the measurement sensitivity S is worked out then from the estimated partial optical path length LF, and the information relating to the amount of substance to be measured is corrected using the measurement sensitivity S.

The above-described method for measuring a scattering-absorption body elicits the following effects. In the present method, specifically, the intervening tissue thickness A can be estimated from the mean optical path length L, and hence information relating to the amount of substance to be measured in the region to be measured B1 can be accurately worked out, even without actually measuring the intervening tissue thickness A using an ultrasonic device or the like. Therefore, it becomes possible to compare information relating to the amount of substance to be measured, without regard to dissimilarities in the intervening tissue thickness A depending on the subject and on the measurement site.

The method and device for measuring a scattering-absorption body according to the present invention are not limited to the above-described embodiments, and can accommodate various modifications. For example, an instance has been explained, in the embodiment above, wherein the present invention is used in a time-resolved measurement method, but the above embodiment can be used for other methods for measuring an mean optical path length, for instance phase difference methods. Even in a method such as a CW method or the like, where an mean optical path length cannot be measured, the measurement results obtained according to such a method can nonetheless be corrected if the mean optical path length L is measured beforehand in accordance with a time-resolved spectroscopy method or the like.

In the above embodiment, an instance has been explained wherein measured values are corrected in real time, but correction may be performed once measurements are over. The correlation between intervening tissue thickness and mean optical path length illustrated in the above embodiment is merely exemplary in nature, and the expressions used for correction can be used in various correction relational expressions. In the above embodiment there is used an mean optical path length that is measured at rest, but the embodiment is not limited to measurements at rest, and it is sufficient that the measurement conditions be met. In the above embodiments, avascularization is used as a method for varying only the substance to be measured in order to measure a pre-correction variation amount in a case where only the concentration of the substance to be measured is caused to vary, as used in the unit optical path length calculating unit 414. However, the method for varying only the substance to be measured is not limited to the above-mentioned one, and the substance to be measured may be caused to vary by using a drug, or by simulation, so long as the above conditions are satisfied.

In the above embodiment an example has been explained wherein hemoglobin (oxyhemoglobin, deoxyhemoglobin and total hemoglobin) is the substance to be measured, but the substance may be any other substance, provided that the latter absorbs light of a predetermined wavelength. In the above embodiment, correction is performed by dividing a calculated blood variation amount by a measurement sensitivity, but a variation amount of the absorption coefficient prior to hemoglobin conversion may also be corrected. The variation amount of the absorption coefficient after correction can then be treated as the hemoglobin after correction, through conversion to hemoglobin.

The correction in the embodiment above applies to the absorption variation amount, but may be treated as a quantitative value, through addition of a relative variation amount to a quantitative value that is obtained from a diffusion equation. Oxygen saturation ($SO_2$) can be calculated accordingly as well.

In the above embodiment, muscle is exemplified as the region to be measured and fat as the intervening tissue, but the region to be measured and the intervening tissue are not limited thereto. The above embodiment may be used in various multilayer-structure tissues, such that, for instance in a measurement of the head, the region to be measured is for instance brain tissue, and the intervening tissue is the skull or the like.

Figure 14:
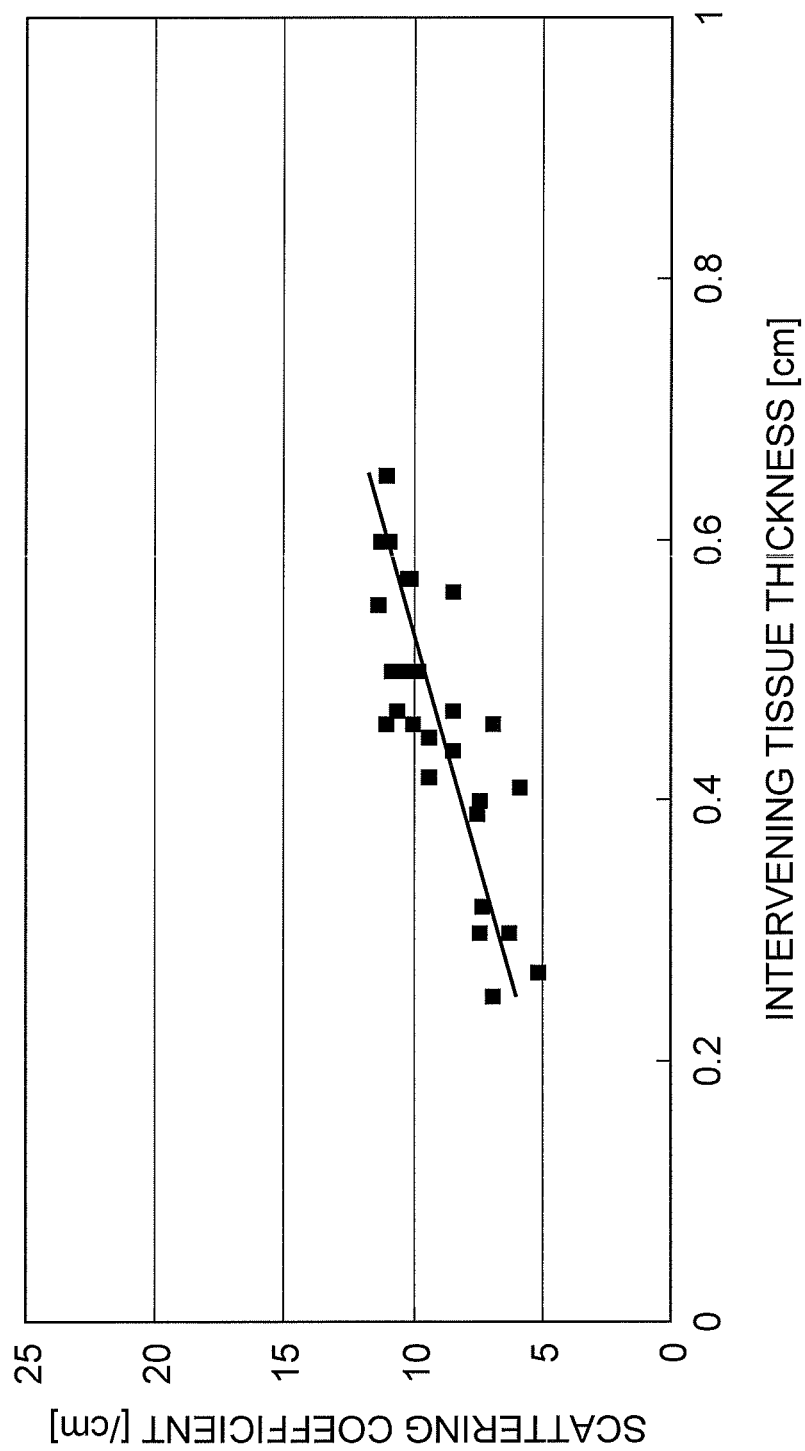
FIG. 14 is a graph illustrating a correlation between scattering coefficients and intervening tissue thickness.
Figure 15:
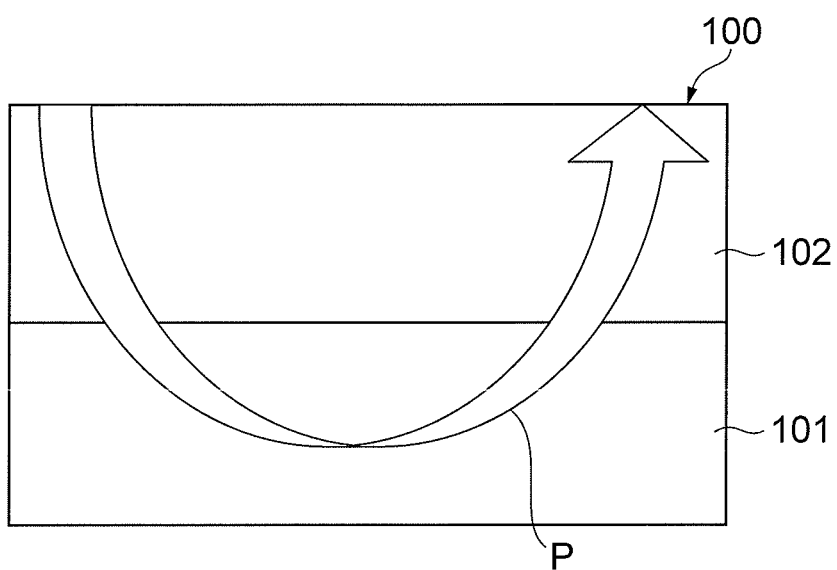
FIG. 15(a) and FIG. 15(b) are diagrams illustrating schematically the internal structure of a scattering-absorption body.
Figure 15:
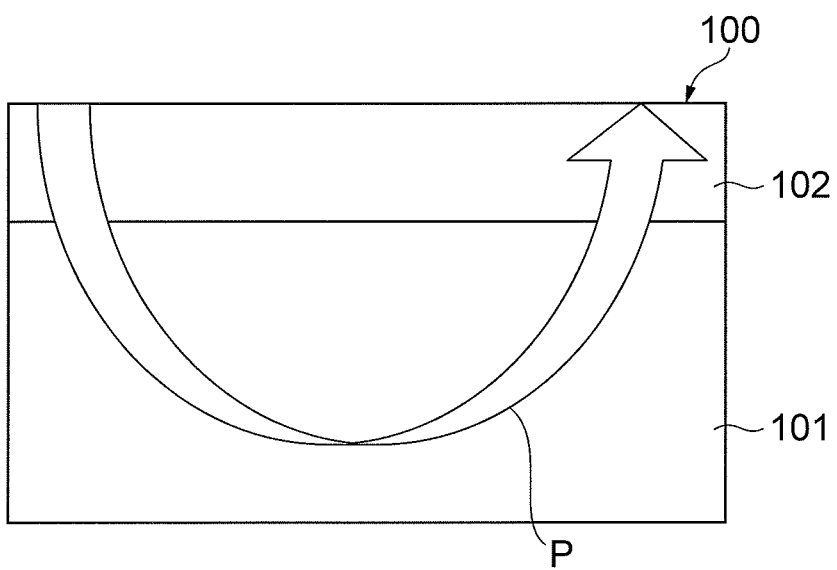

The above embodiment utilizes a relationship between mean optical path length and intervening tissue thickness, but measured values may be corrected by relying on a relationship between scattering coefficients and the intervening tissue thickness, for instance such as the one illustrated in FIG. 14. As FIG. 14 shows, the greater the intervening tissue thickness, the larger becomes the scattering coefficient. The measured value can be appropriately corrected on the basis of such a correlation (or, on the basis of a correlation in which the intervening tissue thickness is replaced by the mean optical path length).

The measurement method according to the embodiment allows estimating the intervening tissue thickness from the mean optical path length. In addition to correcting information relating to the amount of substance to be measured in a region to be measured, it becomes also possible therefore to measure intervening tissue thickness, as an alternative to a conventional method (involving an ultrasonic device or the like) for measuring intervening tissue thickness.

INDUSTRIAL APPLICABILITY

The present invention is useful as a method and device for measuring a scattering-absorption body that enable measurement result, having had the influence of intervening tissue excluded therefrom, to be obtained in accordance with a simple method.

REFERENCE SIGNS LIST

1 . . . device for measuring a scattering-absorption body; 10 . . . light incident means; 11 . . . pulsed light source; 12 . . . light guide for light incidence; 20 . . . light detecting means; 21 . . . light guide for light detection; 22 . . . light detector; 30 . . . signal processing means; 31 . . . temporal profile measuring unit; 40 . . . calculation means; 41 . . . arithmetic processing unit; 50 . . . control unit; 60 . . . main body; 70 . . . display device; 411 . . . pre-correction variation amount calculating unit; 412 . . . mean optical path length calculating unit; 413 . . . intervening tissue thickness calculating unit; 414 . . . unit optical path length calculating unit; 415 . . . partial optical path length calculating unit; 416 . . . measurement sensitivity calculating unit; 417 . . . correction calculating unit; B . . . scattering-absorption body; B1 . . . region to be measured; B2 . . . intervening tissue; Ba . . . surface; D . . . light detecting position; P . . . pulsed light; I . . . light incident position

The invention claimed is:

1. A method for measuring a scattering-absorption body, which is a method for measuring, non-invasively, information relating to an amount of substance to be measured at a region to be measured of a scattering-absorption body that contains the region to be measured and an intervening tissue that is present between the region to be measured and a surface of the scattering-absorption body, the method comprising:

a light incidence step of causing light of a predetermined wavelength to be incident, through one light incident position that is set on the surface of the scattering-absorption body;

a light detection step of obtaining a light detection signal by detecting the light of the predetermined wavelength that propagates through the interior of the scattering-absorption body, at one light detecting position that is set on the surface of the scattering-absorption body;

a signal processing step of acquiring a temporal profile of light intensity of the detected light, on the basis of the light detection signal; and a calculation step of:

calculating, on the basis of the temporal profile, a mean optical path length, and the information relating to the amount of substance to be measured in the region to be measured, the mean optical path length corresponding to passage of the light of the predetermined wavelength through the entire interior of the scattering-absorption body, and calculating a measurement sensitivity corresponding to a ratio of the mean optical path length and an optical path length of a portion of passage through the region to be measured according to an expression $S=LM/L$ where S is the measurement sensitivity, L is the mean optical path length, and LM is the optical path length of a portion of passage through the region to be measured that is within the mean optical path length L, wherein in the calculation step, the information relating to the amount of substance to be measured is corrected by using the measurement sensitivity, and wherein the region to be measured is muscle, and the intervening tissue is fat, or the region to be measured is brain tissue, and the intervening tissue is skull.

2. The method for measuring a scattering-absorption body according to claim 1, wherein in the calculation step, the information relating to the amount of substance to be measured is corrected on the basis of a correlation, acquired beforehand, between the mean optical path length and a thickness of the intervening tissue.

3. The method for measuring a scattering-absorption body according to claim 2, wherein the correlation between the mean optical path length and the thickness of the intervening tissue is a relationship in which the longer the mean optical path length, the thicker the intervening tissue is.

4. The method for measuring a scattering-absorption body according to claim 1, wherein in the calculation step, the information relating to the amount of substance to be measured is corrected on the basis of an optical path length per unit thickness of the intervening tissue acquired beforehand.

5. The method for measuring a scattering-absorption body according to claim 1, wherein in the calculation step, the information relating to the amount of substance to be measured is corrected on the basis of a correlation, acquired beforehand, between the mean optical path length and the measurement sensitivity.

6. The method for measuring a scattering-absorption body according to claim 5, wherein in the calculation step, the correlation between the mean optical path length and the measurement sensitivity is worked out from the mean optical path length and an optical path length of a portion of passage through the region to be measured or the intervening tissue, within the mean optical path length in the interior of the scattering-absorption body.

7. The method for measuring a scattering-absorption body according to claim 1, wherein in the calculation step, the optical path length of a portion of passage through the intervening tissue, within the mean optical path length in the interior of the scattering-absorption body, is estimated on the basis of an optical path length per unit thickness of the intervening tissue, and a thickness of the intervening tissue obtained from a correlation, acquired beforehand, between the thickness of the intervening tissue and the mean optical path length, the measurement sensitivity is worked out from the estimated optical path length, and the information relating to the amount of substance to be measured is corrected using the measurement sensitivity.

8. A device for measuring a scattering-absorption body, which is a device that measures, non-invasively, information relating to an amount of substance to be measured at a region to be measured of a scattering-absorption body that contains the region to be measured and an intervening tissue that is present between the region to be measured and a surface of the scattering-absorption body, the device comprising:
   a light source for causing light of a predetermined wavelength to be incident, through one light incident position that is set on the surface of the scattering-absorption body;
   a light detector for generating a light detection signal by detecting the light of the predetermined wavelength that propagates through the interior of the scattering-absorption body, at one light detecting position that is set on the surface of the scattering-absorption body;
   a signal processor connected to the light detector for acquiring a temporal profile of light intensity of the detected light, on the basis of the light detection signal; and
a calculator connected to the signal processor for:
   calculating, on the basis of the temporal profile, a mean optical path length, and the information relating to the amount of substance to be measured in the region to be measured, the mean optical path length corresponding to passage of the light of the predetermined wavelength through the entire interior of the scattering-absorption body,
   calculating a measurement sensitivity corresponding to a ratio of the mean optical path length and an optical path length of a portion of passage through the region to be measured according to an expression $S=LM/L$ where $S$ is the measurement sensitivity, $L$ is the mean optical path length, and $LM$ is the optical path length of a portion of passage through the region to be measured that is within the mean optical path length $L$, wherein
   the calculator corrects the information relating to the amount of substance to be measured on the basis of the measurement sensitivity, and wherein
   the region to be measured is muscle, and the intervening tissue is fat, or the region to be measured is brain tissue, and the intervening tissue is skull.

9. The device for measuring a scattering-absorption body according to claim 8, wherein the calculator corrects the information relating to the amount of substance to be measured on the basis of a correlation, acquired beforehand, between the mean optical path length and the thickness of the intervening tissue.

10. The device for measuring a scattering-absorption body according to claim 9, wherein the correlation between the mean optical path length and the thickness of the intervening tissue is a relationship in which the longer the mean optical path length, the thicker the intervening tissue is.

11. The device for measuring a scattering-absorption body according to claim 8, wherein the calculator corrects the information relating to the amount of substance to be measured on the basis of an optical path length per unit thickness of the intervening tissue acquired beforehand.

12. The device for measuring a scattering-absorption body according to claim 8, wherein the calculator corrects the information relating to the amount of substance to be measured on the basis of a correlation, acquired beforehand, between the mean optical path length and the measurement sensitivity.

13. The device for measuring a scattering-absorption body according to claim 12, wherein the calculator works out the correlation between the mean optical path length and the measurement sensitivity from the mean optical path length and an optical path length of a portion of passage through the region to be measured or the intervening tissue, within the mean optical path length in the interior of the scattering-absorption body.

14. The device for measuring a scattering-absorption body according to claim 8, wherein the calculator estimates the optical path length of a portion of passage through the intervening tissue, within the mean optical path length in the interior of the scattering-absorption body, on the basis of an optical path length per unit thickness of the intervening tissue and a thickness of the intervening tissue obtained from a correlation, acquired beforehand, between the thickness of the intervening tissue and the mean optical path length, and works out the measurement sensitivity from the estimated optical path length, and moreover corrects the information relating to the amount of substance to be measured using the measurement sensitivity.

* * * * *